United States Patent [19]

Bonham

[11] Patent Number: 4,950,067

[45] Date of Patent: Aug. 21, 1990

[54] HOLOGRAM WHICH HELPS REDUCE EYE STRAIN

[76] Inventor: Celeste V. Bonham, 835 Fernwood Pacific Dr., Topanga, Calif. 90290

[21] Appl. No.: 375,834

[22] Filed: Jul. 5, 1989

[51] Int. Cl.⁵ .......................... A61B 3/00; G03H 1/02

[52] U.S. Cl. .................................... 351/203; 351/246; 350/3.6

[58] Field of Search .................. 350/3.6, 3.7; 351/201, 351/203, 206, 246; 128/25 A

[56] References Cited

U.S. PATENT DOCUMENTS 4,376,950 3/1983 Brown et al. ........................ 350/3.6

*Primary Examiner*—Paul M. Dzierzynski

[57] ABSTRACT

A hologram comprised of two or more opticals (10) which communicate images of depth-of-field; a light source (11) to illuminate said opticals.

2 Claims, 1 Drawing Sheet

HOLOGRAM WHICH HELPS REDUCE EYE STRAIN

BACKGROUND-FIELD OF INVENTION

This invention relates to eye exercising which helps to reduce eye strain; specifically utilizing depth-of-field opticals in a hologram.

BACKGROUND-DISCUSSION OF PRIOR ART

We live in a computer age where computers are becoming more incorporated into our society with every passing year. Our future will become more computerized as technology broadens and the ease for the user is simplified.

This vast growing industry has lead to a very dangerous medical problem: weakening of the eyes due to extended viewing of VDTs (video-display terminals). Eye strain is caused by a few factors. One factor being the constant viewing of a screen, book, or television without taking the time to exercise and "stretch" the eye muscles. This specific exercise occurs when eyes shift focus from far to near and back again thus creating depth-of-field in ones vision.

I experienced the difficulty in focusing of vision after extended use on my computer. An eye doctor informed me to take breaks in my work schedule and exercise my eyes. He suggested that I focus on my thumb and then on the corner in the room not closer than a distance of six feet. (Infinity in eye sight starts at 20 feet). Doing this exercise every 15 to 30 minutes for about 10 to 15 seconds would largely reduce the eye strain I was experiencing. I researched in the library editorial section and found a vast array of articles written in such major publications as: U.S. News & World Report, Forbes, Scientific American, PC — Personal Computing, PC Week, etc. Each of these articles noted the growing problem of eye strain in the work place and especially where computers are being used. Some articles also stated that the increasingly high percentage of children having to where glasses at an earlier age than normal is directly related to eye strain. Research has concluded that children are becoming more indoctrined and educated on computers as technology advances. With the growing attraction to televisions, children are not getting enough eye exercise needed to keep the eyes healthy thus resulting in early eye impairment and the need of eye glasses. We cannot change man's evolution and the advancement of technology, but this simple invention can help to detain the eye impairment among our children.

I have not found an invention in the marketplace which directly aids in this problem. Searching through the patent library I found no prior art or patents utilizing holograms to strengthen the eye muscles through depth-of-field opticals. I searched through Class 350 (Optics Systems & Elements) 3.7 (Using a hologram as an ordinary optical element) and 3.84 (Focused image holography); and through Class 351 (Optics - Eye examining, Vision, Testing & Correcting) 203 (Eye exercising or training type) to no avail. None of the prior art or patents directly (or even came close) utilized holograms to strengthen the eye muscles through depth-of-field opticals.

This invention was created to help reduce eye strain through the use of a hologram which has two or more optical images with depth-of-field value. It will have its own light source to sharpen the opticals, thereby giving stronger and more distinctive images to focus upon.

OBJECTS AND ADVANTAGES

Accordingly, there are several advantages to my invention:

(a) to provide an exercise for the eye muscles which helps to reduce eye strain;

(b) to provide an easily accessible invention for consumers which will help strengthen their eye sight;

(c) to provide an entertaining visual display which will attract the attention of the consumer;

(d) holograms will be designed for individual age groups, thereby attracting its use to a broader age range from young children to adults;

(e) to provide an alternative relaxed visual which will also incorporate a peace of mind and help reduce stress connected with the extended use of VDTs, books, or television;

(f) to provide less stress of the eyes which will reduce headaches and job absenteeism.

Further advantages will become apparent from a consideration of the description described later.

DESCRIPTION

Figure 1:
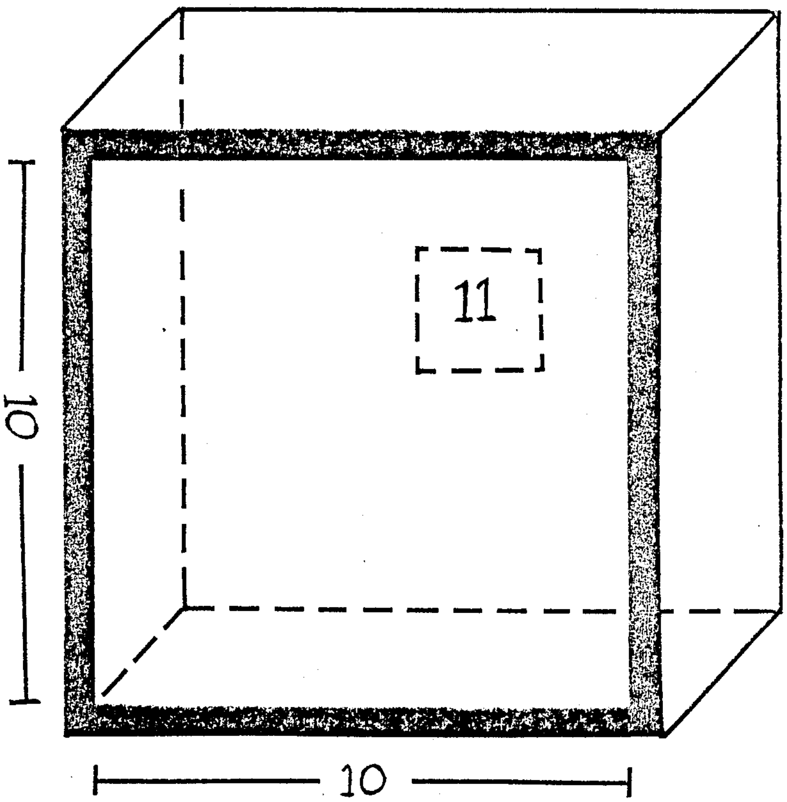
FIG. 1 is a perspective view of my invention.

A hologram is a medium which enables the storage of three-dimensional visual information on a two-dimensional plane. A hologram is not a new invention. It was first invented in 1947 by Dr. Dennis Gabor and has been successfully improved over the years.

The opticals (10) within these holograms will be recorded with laser light on an unexposed emulsion while facing a three-dimensional object. The laser is optically split into two beams on a complex optical vibration isolation table. One beam is used to illuminate the real three-dimensional object while the other beam is directed straight at the emulsion. The film receives the patterns of both objects reflected light resulting in the recording where the beams intersect at the unexposed emulsion. Either a laser or incandescent light source is then positioned thus activating the object to appear in three-dimension. This process will be reproduced two or more times so that within one hologram there will be two or more three-dimensional opticals thereby creating depth-of-field within its visuals.

The hologram will not be less than fifteen meters in diameter. The hologram can be made in any shape (square, circle, rectangular, etc.). The hologram will be displayed in a free standing self-contained display, thus allowing the ability to have its own light source (11). This invention will utilize the transmission type hologram for light source. This type allows the viewing light source (11) to transmit information through the hologram, which is between the viewer and the light source. The light source (11) will be either illuminated through an outside electrical source or self contained batteries. It can have a wide array of optical visuals — the images are limitless with the only prerequisite that there is depth-of-field within the two or more opticals contained within.

OPERATION OF INVENTION

The manner of using the hologram is quite simple. First of all plug in the light source which will illuminate the opticals contained in the hologram. The light source can be illuminated at all times or can be controlled by a switch or button. Focus on the image in the hologram. Once you have a strong focus of the image displayed in the hologram; slightly change the position of your head and eyes and the image will change. Focus on this new image in the hologram. Once you have a strong focus of this image, slightly change the position of your head and eyes and you will return to your first image. The images will be designed to give the viewer depth-of-field. One image will appear to be very close to the viewer, and following shifting the relative position of the viewer's head and the hologram, the image appears to be at a different or at an infinite distance from the viewer. For ten to fifteen seconds continue to focus between these images. Do this once every fifteen to thirty minutes and this exercise will help strengthen and stretch your eye muscles thus helping to reduce eye strain.

CONCLUSION, RAMIFICATIONS, AND SCOPE OF INVENTION

Thus the reader will see that this invention provides a very simple solution to a vast growing problem of eye strain by exercising the eye muscles. This problem has been greatly acknowledged and emphasized within the computer age we live in. The simplicity of the invention allows for this to be a very reasonable and economical devise. Furthermore, it has the additional advantages in that

- it is not limited to one age group but allows children as well as adults to benefit from its use;
- it is easily accessible to the consumer;
- with entertaining, interesting, and relaxing optics, the viewer will be more apt to want to use the invention.

While my above description contains specifications, these should not be construed as limitations on the scope of the invention, but rather as an exemplification of one preferred embodiment thereof. Many other variations are possible. For example: In FIG. 1 it shows one type of display. An alternative display the invention will be able to attach to the computer monitor casing. Ultimately I see this invention being incorporated within a software program so that with a touch of a finger the hologram images will appear on the screen of the monitor.

Accordingly, the scope of the invention should be determined not by the embodiment illustrated, but by the appended claims and their legal equivalents.

I claim:

1. A method of stimulating the eye muscles with a hologram including two or more depth-of-field opticals with one image appearing to be very close to the viewer and one image substantially at an infinite distance from the viewer, comprising the steps of:
   - displaying the hologram;
   - illuminating the hologram;
   - having a viewer strongly focus on one of the images of the hologram appearing to be at one distance from the viewer;
   - shifting the relative position of the viewer's head and the hologram to present to the viewer another image of the hologram appearing to be at a different distance from the viewer and having the viewer strongly focus on this different image, thereby exercising the viewer's eye muscles.

2. A method as defined in claim 1 for use by persons operating video display terminals comprising the additional step of operating the video display terminal for periodic intervals, and then interrupting the operation of the video display terminal and performing the steps of claim 2 for an interval of time before resuming operation of the terminal.

* * * * *